(12) United States Patent
Jacobs et al.

(10) Patent No.: US 7,713,548 B2
(45) Date of Patent: May 11, 2010

(54) AMORPHOUS SOLID DISPERSIONS

(75) Inventors: Irwin C. Jacobs, Eureka, MO (US);
John D. Higgins, Phoenixville, PA (US);
Micael Guillot, Phoenixville, PA (US);
Nancy M. Franson, Collegeville, PA (US); William L. Rocco, Reading, PA (US); Khawla Abdullah Abu-Izza, Highland Mills, NY (US)

(73) Assignee: sanofi-aventis U.S. LLC, Bridgewater, NJ (US)

( * ) Notice: Subject to any disclaimer, the term of this patent is extended or adjusted under 35 U.S.C. 154(b) by 124 days.

(21) Appl. No.: 12/029,691

(22) Filed: Feb. 12, 2008

(65) Prior Publication Data

US 2008/0160080 A1 Jul. 3, 2008

Related U.S. Application Data

(63) Continuation of application No. PCT/US2006/033022, filed on Aug. 24, 2006.

(60) Provisional application No. 60/712,150, filed on Aug. 29, 2005.

(51) Int. Cl.
*A61K 31/503* (2006.01)
*A61K 9/20* (2006.01)

(52) U.S. Cl. .................................. 424/464; 514/248

(58) Field of Classification Search .................. 424/464; 514/248
See application file for complete search history.

(56) References Cited

U.S. PATENT DOCUMENTS

| | | | |
|---|---|---|---|
| 5,091,381 A * | 2/1992 | Kim et al. | 514/183 |
| 6,262,045 B1 | 7/2001 | Evanno et al. | |
| 6,379,649 B1 * | 4/2002 | Katsifis et al. | 424/1.85 |
| 6,395,729 B1 | 5/2002 | Ferzaz et al. | |
| 6,548,555 B1 | 4/2003 | Curatolo et al. | |
| 2004/0013734 A1 | 1/2004 | Babcock et al. | |
| 2005/0031692 A1 | 2/2005 | Beyerinck et al. | |

FOREIGN PATENT DOCUMENTS

| FR | 2829939 | 3/2003 |
|---|---|---|
| WO | WO 2005/034999 | 4/2005 |

OTHER PUBLICATIONS

Ferzaz, B., et. al., SSR180575 (7-Chloro-N,N,5-Trimethyl-4-Oxo-3-Phenyl-3,5-Dihydro-4H-Pyridazino[4,5-b]Indole-1-Acetamide), A Peripheral Benzodiazepine Receptor Ligand, Promotes Neuronal Survival and Repair, The Journal of Pharmacology and Experimental Therapeutics, vol. 301, No. 3, pp. 1067-1078 (2002).

Galiegue, S., et. al., The Peripheral Benzodiazepine Receptor: A Promising Therapeutic Drug Target, Current Medicinal Chemistry, vol. 10, No. 16, (2003)—pp. 1563-1572.

Hancock et al, What is the True Solubility Advantage for Amorphous Pharmaceuticals?, Pharmaceutical Research, vol. 17, No. 4, pp. 397-404 (2000).

Kai et al, Oral Absorption Improvement of Poorly Soluble Drug Using Solid dispersion Technique, Chem. Pharm. Bull. 44(3) pp. 568-571 (1996).

Leuner et al, Improving Drug Solubility for Oral Delivery Using Solid Dispersions, EJPB 50 (2000) pp. 47-60.

Serajuddin, Solid Dispersion of Poorly Water-Soluble Drugs: Early Promises, Subsequent Problems, and Recent Breakthroughs, Journal of Pharmaceutical Sciences vol. 88, No. 10, pp. 1058-1066, Oct. 1999.

Tanno et al, Evaluation of Hypromellose Acetate Succinate (HPMCAS) as a Carrier in Solid Dispersions, Drug Development and Industrial Pharmacy vol. 30, No. 1, pp. 9-17, 2004.

* cited by examiner

*Primary Examiner*—Robert A Wax
*Assistant Examiner*—Aradhana Sasan
(74) *Attorney, Agent, or Firm*—Kelly L. Bender

(57) ABSTRACT

Disclosed are amorphous solid dispersion formulations comprising 7-chloro-N,N,5-trimethyl-4-oxo-3-phenyl-3,5-dihydro-4H-pyridazino[4,5-b]indole-1-acetamide.

33 Claims, 11 Drawing Sheets

AMORPHOUS SOLID DISPERSIONS

CROSS REFERENCE TO RELATED APPLICATIONS

This application is a continuation of International application No. PCT/US2006/033,022, filed Aug. 24, 2006; which claims the benefit of priority of U.S. Provisional Application No. 60/712,150, filed Aug. 29, 2005, both of which are incorporated herein by reference in their entirety.

BACKGROUND OF THE INVENTION

1. Field of the Invention

The present invention relates to amorphous solid dispersions of 7-chloro-N,N,5-trimethyl-4-oxo-3-phenyl-3,5-dihydro-4H-pyridazino[4,5-b]indole-1-acetamide, a pharmacological agent possessing a high affinity for the peripheral-type benzodiazepine receptors.

This invention also relates to processes for the preparation of these amorphous solid dispersions, to pharmaceutical compositions including such dispersions, and to methods of use thereof for the prevention and treatment of diseases related to peripheral-type benzodiazepine receptors.

2. Description of the Art

7-Chloro-N,N,5-trimethyl-4-oxo-3-phenyl-3,5-dihydro-4H-pyridazino[4,5-b]indole-1-acetamide, which has the structure of Formula (I):

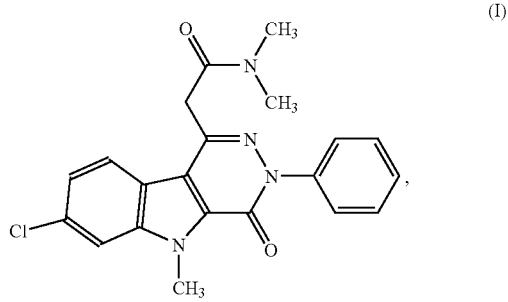

(I)

possesses a high affinity for the peripheral-type benzodiazepine receptors. The preparation, physical properties and beneficial pharmacological properties of 7-chloro-N,N,5-trimethyl-4-oxo-3-phenyl-3,5-dihydro-4H-pyridazino[4,5-b]indole-1-acetamide are described in, for example, U.S. Pat. No. 6,262,045 and, in particular, U.S. Pat. No. 6,395,729, both of which are incorporated by reference in their entirety The limited solubility of crystalline 7-chloro-N,N,5-trimethyl-4-oxo-3-phenyl-3,5-dihydro-4H-pyridazino[4,5-b]indole-1-acetamide, prepared according to Example 1 of U.S. Pat. No. 6,395,729, in both aqueous solutions and non-aqueous formulation solvents presents difficulties in the administration and storage of formulations containing this compound. Preliminary studies carried out with conventional formulations using this crystalline solid (such as formulations prepared by wet granulation or dry blend processes using standard excipients well known to those of skill in the art) have led to limited absorption of the drug.

Attempts to improve the solubility of the pure drug substance, such as by preparing and utilizing amorphous forms of 7-chloro-N,N,5-trimethyl-4-oxo-3-phenyl-3,5-dihydro-4H-pyridazino[4,5-b]indole-1-acetamide, resulted in drug substance with limited physical stability. For example, such drug substance crystallized over time.

It has now been found that certain polymers are useful for preparing dispersions of solid amorphous 7-chloro-N,N,5-trimethyl-4-oxo-3-phenyl-3,5-dihydro-4H-pyridazino[4,5-b]indole-1-acetamide having significant solubility improvements over conventional formulations and also possessing significant physical stability improvements over amorphous drug substance alone. Solid amorphous dispersions of poorly soluble drugs in polymers are known generally to improve the solubility of drug products. However, such dispersions are generally unstable over time. Amorphous dispersions of drugs in polymers tend to convert to crystalline forms over time, which can lead to improper dosing due to differences of the bioavailability and solubility of crystalline drug material compared to amorphous drug material. One skilled in the art cannot predict which polymers, if any, would be useful for preparing stable amorphous dispersions for a particular drug product. The present invention, however, provides such stable amorphous dispersions with improved solubility.

SUMMARY OF TIE INVENTION

The present invention provides stable amorphous solid dispersions of the active agent, 7-chloro-N,N,5-trimethyl-4-oxo-3-phenyl-3,5-dihydro-4H-pyridazino[4,5-b]indole-1-acetamide.

The present invention also provides processes for preparing and to compositions comprising the amorphous solid dispersions of the instant invention, and to methods of use thereof.

DETAILED DESCRIPTION OF THE INVENTION

Definitions and Abbreviations

Figure 1:
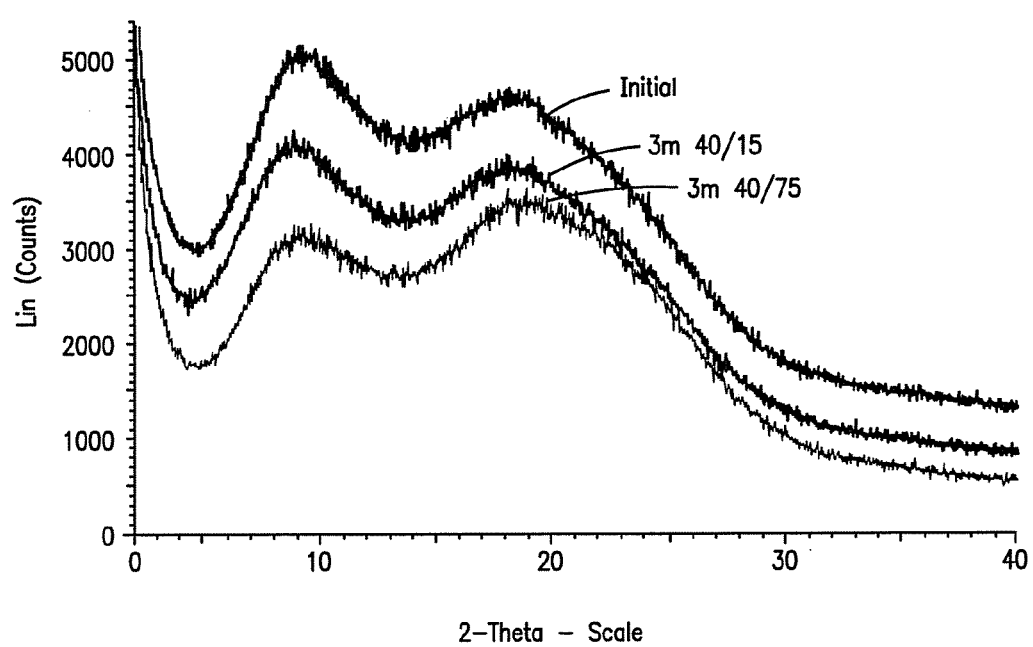
FIG. 1 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in hydroxypropyl methylcellulose phthalate under stressed and unstressed conditions.
Figure 2:
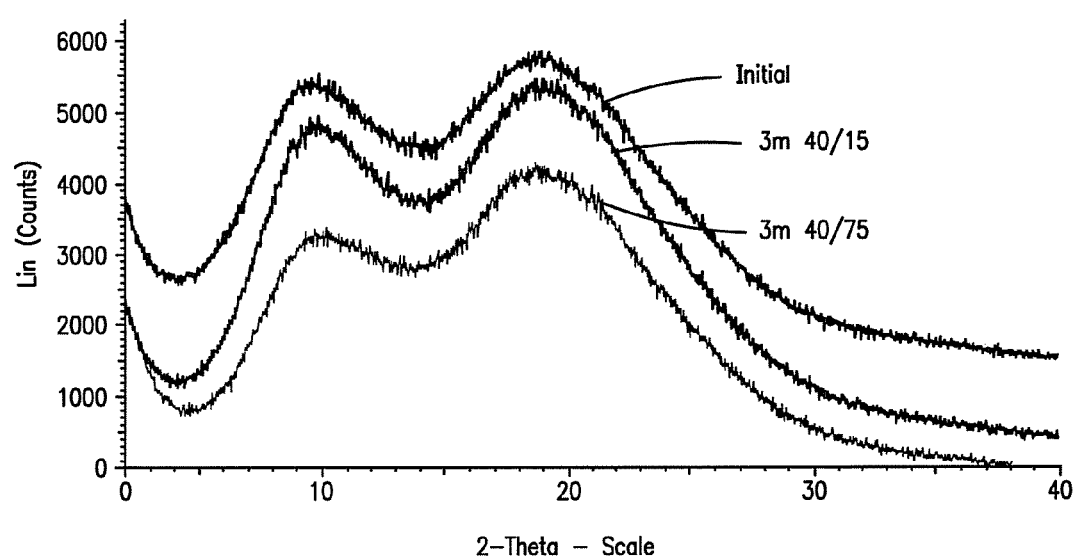
FIG. 2 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in hydroxypropyl methyl cellulose acetate succinate under stressed and unstressed conditions.
Figure 3:
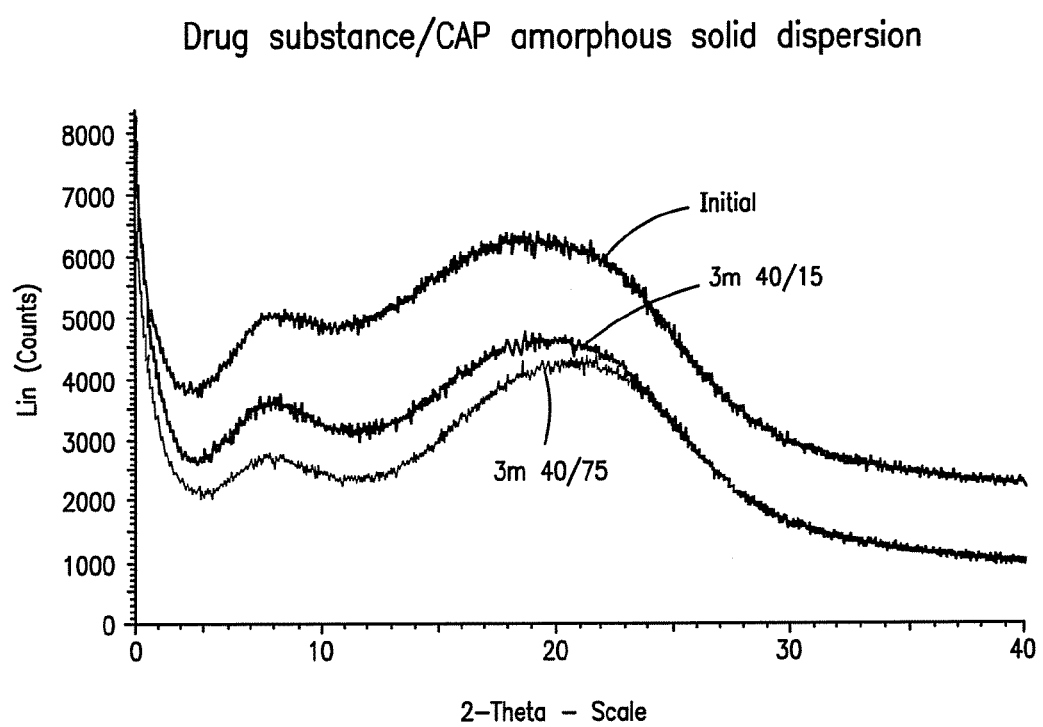
FIG. 3 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in cellulose acetate phthalate under stressed and unstressed conditions.
Figure 4:
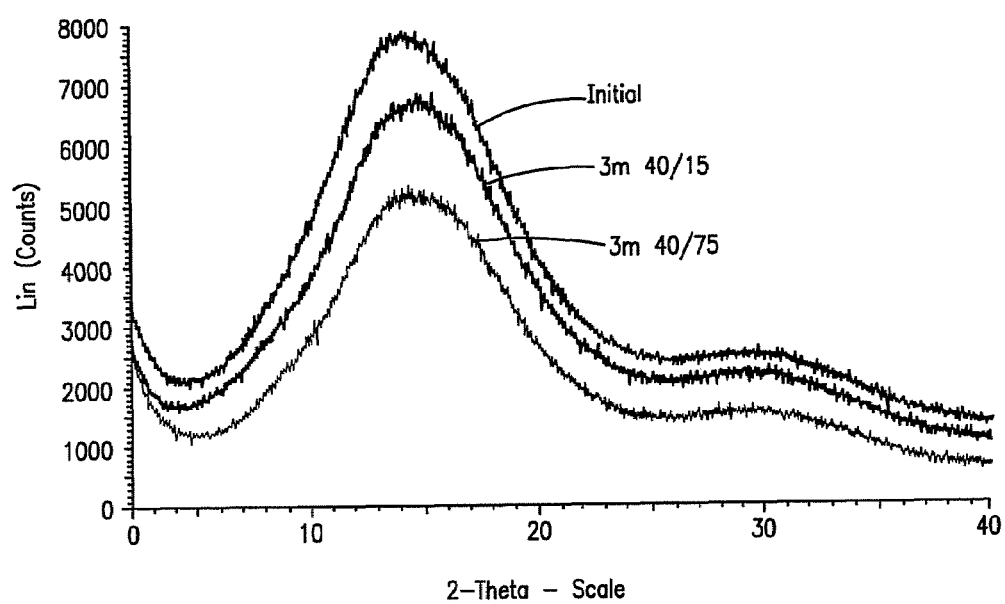
FIG. 4 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in the polymeric polymethacrylate, EUDRAGIT® L 100, under stressed and unstressed conditions.
Figure 5:
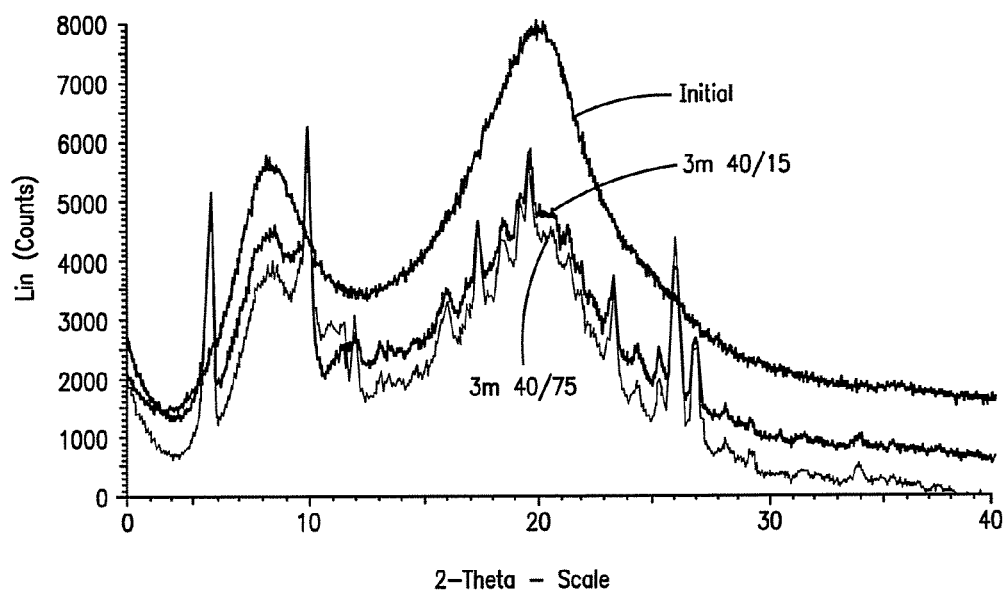
FIG. 5 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in hydroxypropylcellulose under stressed and unstressed conditions.
Figure 6:
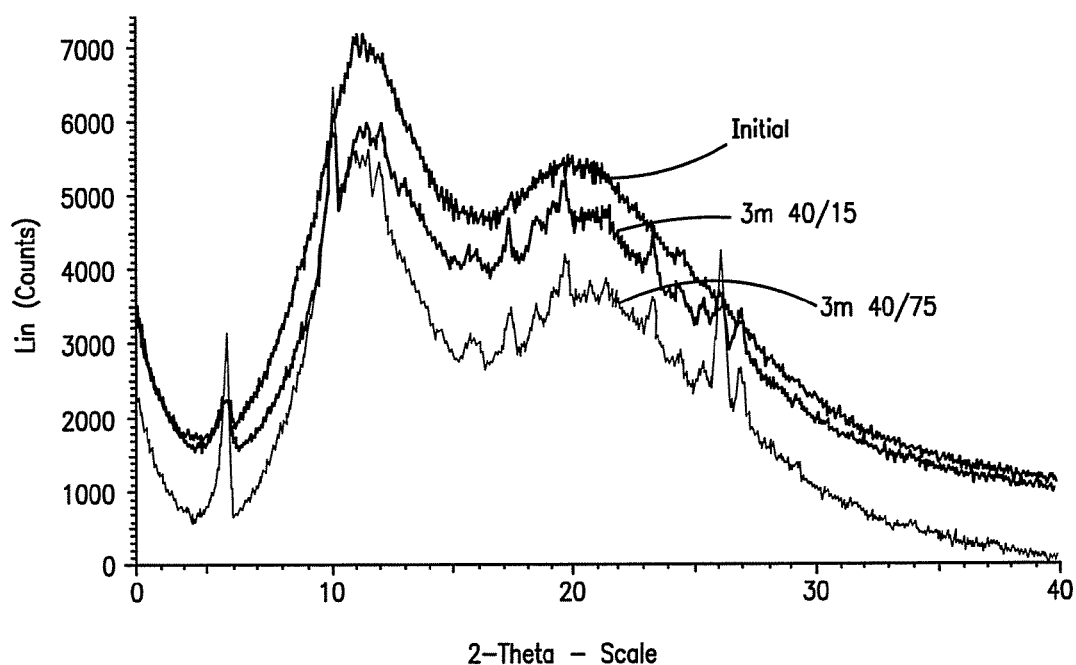
FIG. 6 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in polyvinylpyrrolidone under stressed and unstressed conditions.
Figure 7:
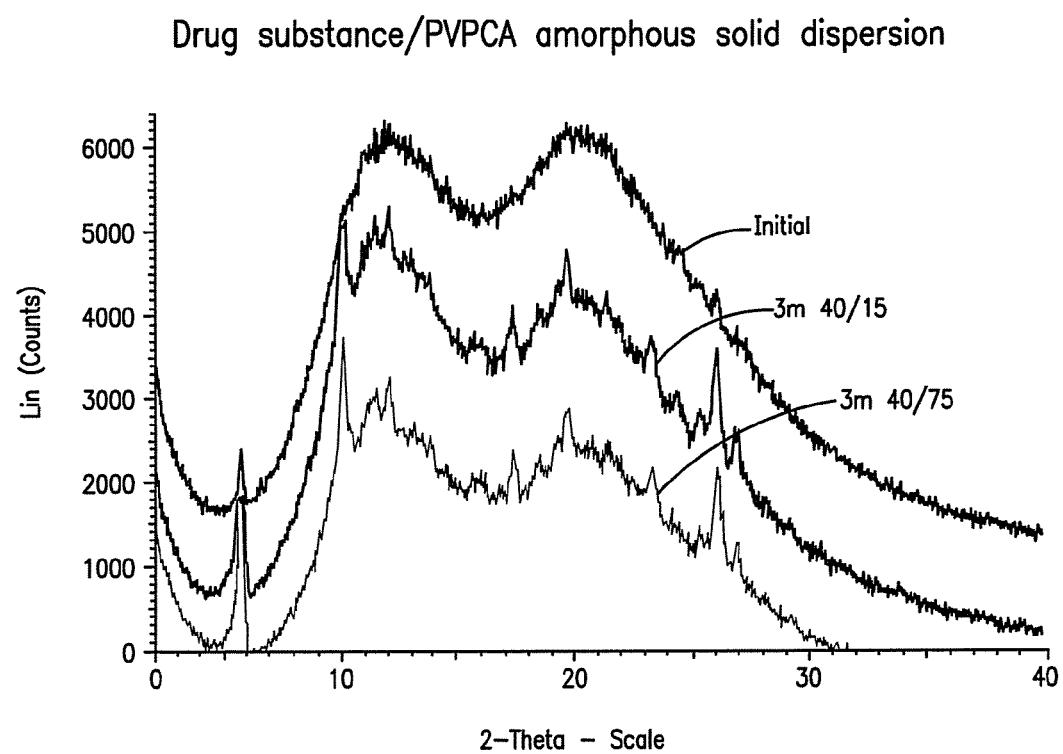
FIG. 7 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in polyvinylpyrrolidone plus 10% citric acid under stressed and unstressed conditions.
Figure 8:
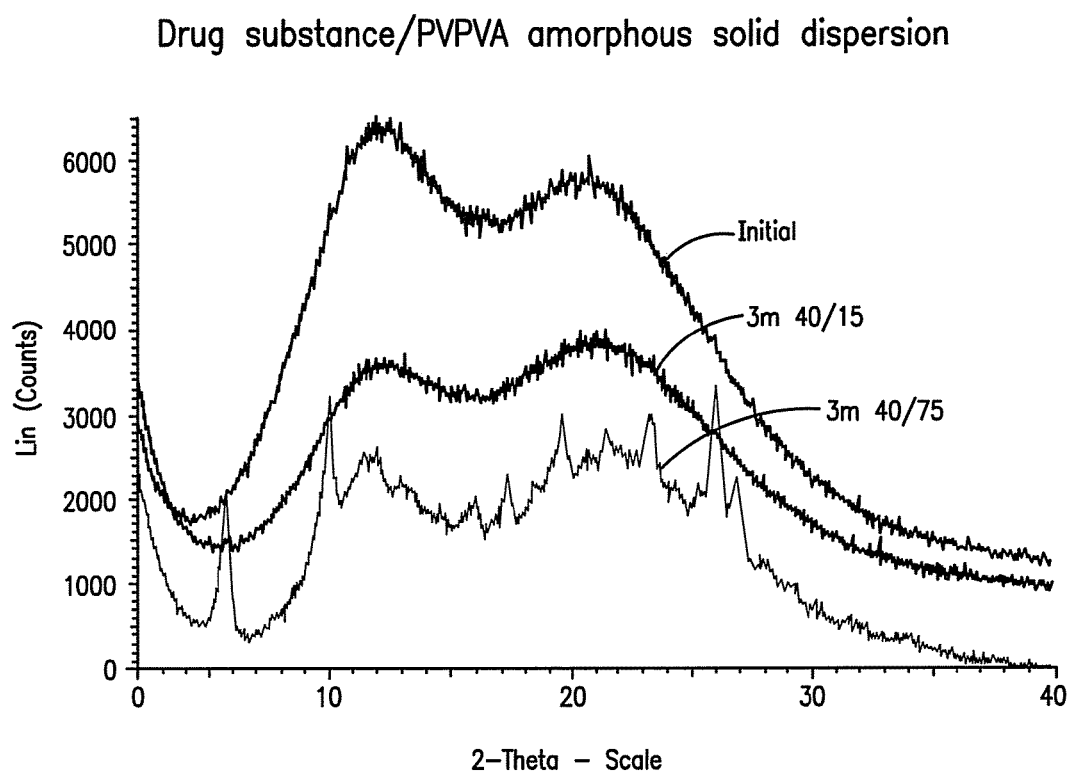
FIG. 8 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in polyvinylpyrrolidone-vinyl acetate copolymer under stressed and unstressed conditions.
Figure 9:
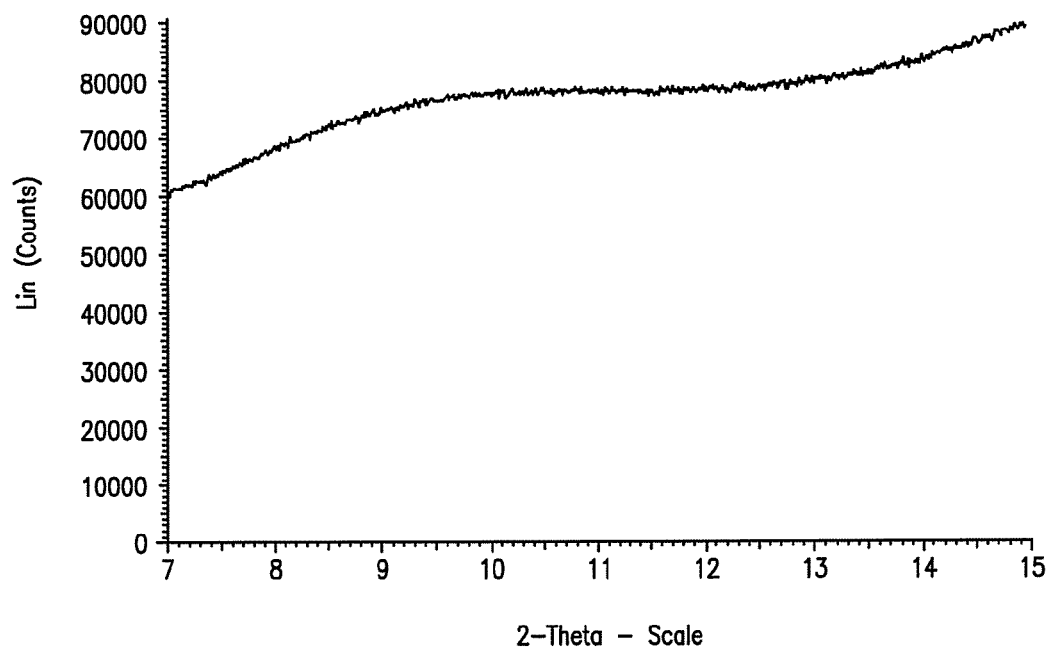
FIG. 9 is an X-ray powder diffractogram of an amorphous solid dispersion of 7-chloro-N,N,5-trimethyl-4-oxo-3-phenyl-3,5-dihydro-4H-pyridazino[4,5-b]indole-1-acetamide in hydroxypropyl methylcellulose phthalate.

As used above, and throughout the description of the invention, the following abbreviations, unless otherwise indicated, shall be understood to have the following meanings:
CAP cellulose acetate phthalate
CA citric acid
DCM dichloromethane
EtOH ethanol
HPC hydroxypropyl cellulose
HPMCAS hydroxypropyl methyl cellulose acetate succinate
HPMCP hydroxypropyl methylcellulose phthalate
PVP polyvinylpyrrolidone As used above, and throughout the description of the invention, the following terms, unless otherwise indicated, shall be understood to have the following meanings:

The term "drug substance," as used herein, refers to 7-chloro-N,N,5-trimethyl-4-oxo-3-phenyl-3,5-dihydro-4H-pyridazino[4,5-b]indole-1-acetamide.

In general, the term "solid dispersion" refers to a system in a solid state comprising at least two components, wherein one component is dispersed throughout the other component or components. The term "amorphous solid dispersion" as used herein, refers to stable solid dispersions comprising amorphous drug substance and a stabilizing polymer. By "amorphous drug substance," it is meant that the amorphous solid dispersion contains drug substance in a substantially amorphous solid state form, that is at least 80% of the drug substance in the dispersion is in an amorphous form. More preferably at least 90% and most preferably at least 95% of the drug substance in the dispersion is in amorphous form.

A solid that is in the "amorphous" solid state form means that it is in a non-crystalline state. Amorphous solids generally possess crystal-like short range molecular arrangement, but no long range order of molecular packing as are found in crystalline solids. The solid state form of a solid, such as the drug substance in the amorphous dispersion, may be determined by Polarized Light Microscopy, X-Ray Powder Diffraction (XPRD), Differential Scanning Calorimetry (DSC), or other standard techniques known to those of skill in the art.

The amount of drug substance in the amorphous dispersions of the present invention ranges from about 0.1% to about 30% by weight relative to the stabilizing polymer. In a preferred embodiment, the amount of drug substance ranges from about 1% to about 25%, more preferably from about 5% to about 20%, by weight relative to the stabilizing polymer.

The term "stabilizing polymer" as used herein, including the claims, refers to any one of hydroxypropyl methylcellulose phthalate (also known as HPMCP and/or hypromellose phthalate), cellulose acetate phthalate (also known as CAP), hydroxypropyl methyl cellulose acetate succinate (also known as HPMCAS) and polymeric polymethacrylates, such as EUDRAGIT® L 100. The term shall also be understood to mean mixtures of any two or more of the aforementioned polymers. Preferred polymers of the invention include hydroxypropyl methylcellulose phthalate, cellulose acetate phthalate, and polymeric polymethacrylate.

In particularly preferred amorphous dispersions of the present invention, the drug substance is present in an amount of from about 5% to about 20% by weight relative to the stabilizing polymer and the stabilizing polymer is hydroxypropyl methylcellulose phthalate.

The amorphous solid dispersions are preferably prepared by dissolving the drug substance and the stabilizing polymer in a suitable solvent to form a feed solution and then spray drying the feed solution to form the amorphous solid dispersion as a powder. A "suitable solvent," as used herein, is a solvent or mixture of solvents in which both the drug substance and the polymer have adequate solubility, e.g. solubility that is greater than about 1 mg/ml. A mixture of solvents is preferred if the drug substance and stabilizing polymer require different solvents to obtain the desired solubility. Examples of suitable solvents include dichloromethane, chloroform, ethanol, methanol, 2-propanol, ethylacetate, acetone, water or mixtures thereof. A preferred solvent is a mixture of dichloromethane and ethanol.

Spray drying is a process well known to those skilled in the art for preparing solid dispersions. In a preferred spray drying process of the present invention, the amorphous dispersion is formed by dispersing or dissolving the drug substance and the stabilizing polymer in a suitable solvent to form a feed solution, pumping the feed solution through an atomizer into a drying chamber, and removing the solvent to form the amorphous solid dispersion powder in the drying chamber. A drying chamber uses hot gases, such as forced air, nitrogen, nitrogen-enriched air, or argon to dry particles. The feed solution can be atomized by conventional means well known in the art, such as a two-fluid sonicating nozzle and a two-fluid non-sonicating nozzle.

Although the amorphous dispersions of the present invention are preferably prepared using conventional spray drying techniques, it will be understood that suitable amorphous solid dispersions may be formed utilizing other conventional techniques known to those skilled in the art, such as melt extrusion, freeze drying, rotary evaporation, drum drying, or other solvent removal process.

In another aspect of the invention, pharmaceutically acceptable excipients generally used in the art are combined with the isolated amorphous solid dispersion powder to form a pharmaceutical composition. Such pharmaceutically acceptable excipients may include one or more fillers; diluents, for example microcrystalline cellulose, lactose, mannitol, pregelatinized starch and the like; disintegrants, for example, sodium starch glycolate, crospovidone, croscarmellose sodium and the like; lubricants, for example, magnesium stearate, sodium stearyl fumarate and the like; sweeteners, for example, sucrose, saccharin and the like; flavoring agents, for example, peppermint, methyl salicylate, orange flavoring and the like; colorants; preservatives; buffers; and/or other excipients depending on the dosage form used.

The pharmaceutical compositions of the present invention preferably contain a therapeutically effective amount of the drug substance. The term "therapeutically effective amount," as used herein, refers to an amount of the drug substance present in the amorphous dispersion or pharmaceutical composition being administered that is sufficient to prevent development of or alleviate to some extent one or more of the symptoms of the disease being treated. Likewise, a therapeutically effective amount of a pharmaceutical composition refers to an amount of such composition that is sufficient to prevent development of, or alleviate to some extent, one or more of the symptoms of the disease being treated. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular dispersion being administered; the mode of administration; the bioavailability characteristics of the preparation administered; the dose regimen selected; the use of concomitant medication; and other relevant circumstances.

The pharmaceutical compositions of the present invention are generally administered orally to patients, which include, but are not limited to, mammals, for example, humans, in the form of, for example, a hard or soft gelatin capsule, a tablet, a caplet, pills, granules or a suspension.

In another embodiment, the present invention relates to dosage forms comprising the pharmaceutical compositions described herein. Dosage forms include, but are not limited to, those selected from the group consisting of pills, hard or soft capsules, caplets, tablets, granules, and suspensions. Each dosage should contain the quantity of drug substance calculated to produce the desired therapeutic effect. Typically, the pharmaceutical compositions will be administered in dosage units containing from about 2 mg to about 2000 mg of the drug substance by weight of the composition, with a range of about 10 mg to about 1000 mg being preferred.

It will also be apparent to those skilled in the art that the pharmaceutical compositions of the present invention can be administered with other therapeutic and/or prophylactic agents and/or medicaments that are not medically incompatible therewith.

All components of the present compositions must be pharmaceutically acceptable. As used herein, a "pharmaceutically acceptable" component is one that is suitable for use with humans and/or other animals without undue adverse side effects (such as toxicity, irritation and allergic response) commensurate with a reasonable benefit/risk ratio.

The present invention further relates to the use of the pharmaceutical compositions of the invention in medicine.

7-Chloro-N,N,5-trimethyl-4-oxo-3-phenyl-3,5-dihydro-4H-pyridazino[4,5-b]indole-1-acetamide is a selective and potent peripheral benzodiazepine receptor (PBR) ligand, and, as such, can be used for the prevention or treatment of peripheral neuropathies of different types, such as trauma-related or ischemic neuropathies, infectious, alcohol-related, drug-related or genetic neuropathies, as well as motoneuron conditions such as spinal amyotrophies and amyotrophic lateral sclerosis.

7-Chloro-N,N,5-trimethyl-4-oxo-3-phenyl-3,5-dihydro-4H-pyridazino[4,5-b]indole-1-acetamide may also be used for the prevention or treatment of neurodegenerative diseases of the central nervous system, either of the acute type such as cerebrovascular accidents and cranial and medullary traumas, or of the chronic type such as autoimmune diseases (multiple sclerosis), Alzheimer's disease, Parkinson's disease and other diseases in which the administration of neurotrophic factors is expected to have a therapeutic effect.

7-Chloro-N,N,5-trimethyl-4-oxo-3-phenyl-3,5-dihydro-4H-pyridazino[4,5-b]indole-1-acetamide may also be used for the prevention or treatment of acute or chronic renal insufficiency, glomerulonephritis, diabetic nephropathy; for the treatment or prevention of cardiac disease or disorder such as chronic heart failure, cardiac ischemia and insufficiency, myocardial infarction, ischemia of the lower limbs, coronary vasospasm, angina pectoris, pathological conditions associated with the cardiac valves, inflammatory cardiac diseases, side effects due to cardiotoxic medicaments or to the aftereffects of cardiac surgery, atherosclerosis and its thromboembolic complications, restenosis, graft rejections, conditions linked to incorrect proliferation or migration of the smooth muscle cells.

7-Chloro-N,N,5-trimethyl-4-oxo-3-phenyl-3,5-dihydro-4H-pyridazino[4,5-b]indole-1-acetamide has shown pharmacological activity in animal models of rheumatoid arthritis by modulating the immune response, and is therefore also useful for the prevention or treatment of rheumatoid arthritis.

Literature data indicates that the peripheral-type benzodiazepine receptor could play a fundamental role in regulating cell proliferation and cancerization processes. In general, and in comparison with normal tissues, an increased density of peripheral-type benzodiazepine receptors is observed in various types of tumors and cancer. Therefore, 7-chloro-N,N,5-trimethyl-4-oxo-3-phenyl-3,5-dihydro-4H-pyridazino[4,5-b]indole-1-acetamide may also be used for the prevention or treatment of tumors and cancers.

The peripheral-type benzodiazepine receptors are also present in the skin and, by virtue of these, 7-chloro-N,N,5-trimethyl-4-oxo-3-phenyl-3,5-dihydro-4H-pyridazino[4,5-b]indole-1-acetamide may be used for the prophylaxis or the treatment of cutaneous stresses. The expression cutaneous stress is understood to mean the various situations which could cause damage in particular in the epidermis, regardless of the agent causing this stress. This agent may be inside and/or outside the body, such as a chemical or free-radical agent, or else outside, such as ultraviolet radiation.

The present invention, therefore, relates to a method of treating and/or preventing diseases related to peripheral-type benzodiazepine receptors, which comprises administering to a patient in need of such treatment or prevention a therapeutically effective amount of an amorphous dispersion of the present invention or a therapeutically effective amount of a pharmaceutical composition of the present invention.

In one embodiment, the present invention relates to a method of treating or preventing a neurodegenerative disease, which comprises administering to a patient in need of such treatment or prevention a therapeutically effective amount of an amorphous dispersion of the present invention or a therapeutically effective amount of a pharmaceutical composition of the present invention.

Another embodiment of the present invention is a method of treating or preventing neuropathy, which comprises administering to a patient in need of such treatment or prevention a therapeutically effective amount of an amorphous dispersion of the present invention or a therapeutically effective amount of a pharmaceutical composition of the present invention.

In another embodiment, the present invention relates to a method of treating or preventing cancer or tumors, which comprises administering to a patient in need of such treatment or prevention a therapeutically effective amount of an amorphous dispersion of the present invention or a therapeutically effective amount of a pharmaceutical composition of the present invention.

Another embodiment of the invention is a method of treating or preventing cutaneous stresses, which comprises administering to a patient in need of such treatment or prevention a therapeutically effective amount of an amorphous dispersion of the present invention or a therapeutically effective amount of a pharmaceutical composition of the present invention.

A preferred embodiment of the invention is a method of treating or preventing rheumatoid arthritis, which comprises administering to a patient in need of such treatment or prevention a therapeutically effective amount of an amorphous dispersion of the present invention or a therapeutically effective amount of a pharmaceutical composition of the present invention.

Another preferred embodiment of the invention is a method for treating or preventing cardiac disease or a cardiac disorder, which comprises administering to a patient in need of such treatment or prevention a therapeutically effective amount of an amorphous dispersion of the present invention or a therapeutically effective amount of a pharmaceutical composition of the present invention.

A subject of the present invention is the use of an amorphous solid dispersion of the present invention in the manufacture of medicinal products for the treatment of diseases related to peripheral-type benzodiazepine receptors, such as neurodegenerative diseases, neuropathies, cancer or tumors, cutaneous stresses, cardiac diseases or cardiac disorders, or rheumatoid arthritis.

The following examples will further illustrate the invention, without, however, limiting it thereto.

EXAMPLE 1

Preparation of an Amorphous Dispersion of 20% Drug Substance in Hydroxypropyl Methylcellulose Phthalate 3.2 grams of hydroxypropyl methylcellulose phthalate (HPMCP, commercially available as HP-55, Shin-Etsu Chemical. Co. Ltd., Tokyo, Japan) and 0.8 g of drug substance (which can be prepared by methods known in art, for example as described in U.S. Pat. No. 6,395,729) were added to a mixture of 72 ml of dichloromethane (DCM) and 72 ml of ethanol (EtOH). The resulting clear feed solution was pumped through an ultrasonic atomizer (commercially available from Sonotek, operated at a frequency of 60 Hz in top spray mode with an inlet gas temperature of 20° C. and an outlet gas temperature of 18° C.) into a drying chamber using a Harvard syringe pump at a feed rate of 2.2 ml/min. The solvent was removed to provide an amorphous solid dispersion.

EXAMPLES 2 to 4

The amorphous solid dispersions of Examples 2, 3, and 4 were prepared essentially according to the procedure described in Example 1, above, using the parameters listed in Table 1.

TABLE 1

Amorphous Dispersions

| Ex. # | Amount of drug substance (g) | Polymer type | Amount of polymer (g) | Solvent system | Inlet temp. (° C.) | Outlet temp. (° C.) | Feed rate (ml/min) |
|---|---|---|---|---|---|---|---|
| 2 | 0.8 | hydroxypropyl methyl cellulose acetate succinate (HPMCAS, Shin-Etsu Chemical. Co. Ltd., Tokyo, Japan | 3.2 | 72 ml DCM and 72 ml EtOH | 20 | 18 | 2.25 |
| 3 | 0.8 | cellulose acetate phthalate (CAP, Eastman Chemical, Kingsport, Tenn.) | 3.2 | 72 ml DCM and 72 ml EtOH | 20 | 18 | 2.25 |
| 4 | 0.8 | polymeric polymethacrylate (commercially available as EUDRAGIT ® L 100, Degussa, Germany | 3.2 | 72 ml DCM and 72 ml EtOH | 20 | 18 | 2.25 |

COMPARATIVE EXAMPLES 5 to 8

The amorphous solid dispersions of Comparative Examples 5, 6, 7, and 8 were prepared essentially according to the procedure described in Example 1, above, using the parameters listed in Table 2.

TABLE 2

Comparative Amorphous Dispersions

| Comp. Ex. # | Amount of drug substance (g) | Polymer type | Amount of polymer (g) | Solvent system | Inlet temp. (° C.) | Outlet temp. (° C.) | Feed rate (ml/min) |
|---|---|---|---|---|---|---|---|
| 5 | 0.8 | hydroxypropylcellulose (HPC, Klucel ® EF, Hercules Incorporated, Wilmington, Del., USA) | 3.2 | 72 ml DCM and 72 ml EtOH | 20 | 18 | 2.25 |
| 6 | 0.8 | Polyvinylpyrrolidone (PVP, commercially available as Plasdone ® K-25, International Specialty Products, Technologies, Wayne, NJ) | 3.2 | 72 ml DCM and 72 ml EtOH | 20 | 18 | 2.25 |
| 7 | 0.8 | Polyvinylpyrrolidone (commercially available as Plasdone ® K-25) plus 10% Citric acid | 3.2 | 72 ml DCM and 72 ml EtOH | 20 | 18 | 2.25 |
| 8 | 0.8 | polyvinylpyrrolidone-vinyl acetate copolymer (PVPVA, commercially available as Kollidon ® VA 64, BASF, Germany) | 3.2 | 72 ml DCM and 72 ml EtOH | 20 | 18 | 2.25 |

EXAMPLE 9

20% Amorphous Drug Substance Dispersed in HPMCP

Hydroxypropyl methylcellulose phthalate (about 400 g) and the drug substance (about 100 g) were added to a mixture of dichloromethane (about 3.56 L) and ethanol (about 3.55 L). The resulting clear feed solution was pumped through a two-fluid nozzle atomizer with an inlet gas temperature of 44° C. and an outlet gas temperature of 25° C. and into a drying chamber at a feed rate of approximately 35 g/min. The solvent was removed to provide about 500 g of the amorphous dispersion wherein the product composition was 20% drug substance/80% HPMCP (HP-55).

Experimentals

X-Ray Power Diffractometry (XRPD) (FIGS. 1 to 9)

XRPD patterns of Examples 1 to 4 and 9 (FIGS. 1 to 4 and 9, respectively) and Comparative Examples 5 to 8 (FIGS. 5 to 8, respectively) were obtained with a Bruker D8® ADVANCE X-ray powder diffractometer using copper K-alpha radiation. The instrument was equipped with parallel beam optics, and the tube voltage and amperage were set to 40 kV and 40 mA, respectively. Samples were scanned at a rate of either 0.1 degrees/minute or 1.0 degree/minute in angle 2-theta.

The initial (non-stressed) XRPD patterns obtained for Examples 1 to 4 and 9 and Comparative Examples 5 to 8 all indicate that the drug substance is substantially in amorphous form.

Stability Studies (FIGS. 1 to 8)

The stabilities of Examples 1 to 4 and Comparative Examples 5 to 8 were determined after storage of samples at 40° C./15% relative humidity for three months. Additional samples were also stored in a high humidity chamber at 40° C./75% relative humidity for three months. A sodium chloride saturated aqueous solution was used to generate the desired humidity for the high humidity chamber. The amorphous solid dispersions were filled into size 0 hard gelatin capsules, then placed in high density polyethylene bottles, which were placed in the chamber at 40° C.

FIGS. 1 to 8 show the XRPD patterns for the examples obtained initially, after 3 months at 40° C./15% relative humidity, and after 3 months at 40° C./75% relative humidity. These patterns indicate that Examples 1 to 4 (FIGS. 1 to 4) unpredictably remained stable (i.e. did not appreciably crystallize) even under stressing conditions, whereas Comparative Example 5 to 8 began to crystallize under stressing conditions, as shown in the XRPD patterns of FIGS. 5 to 8.

Figure 10:
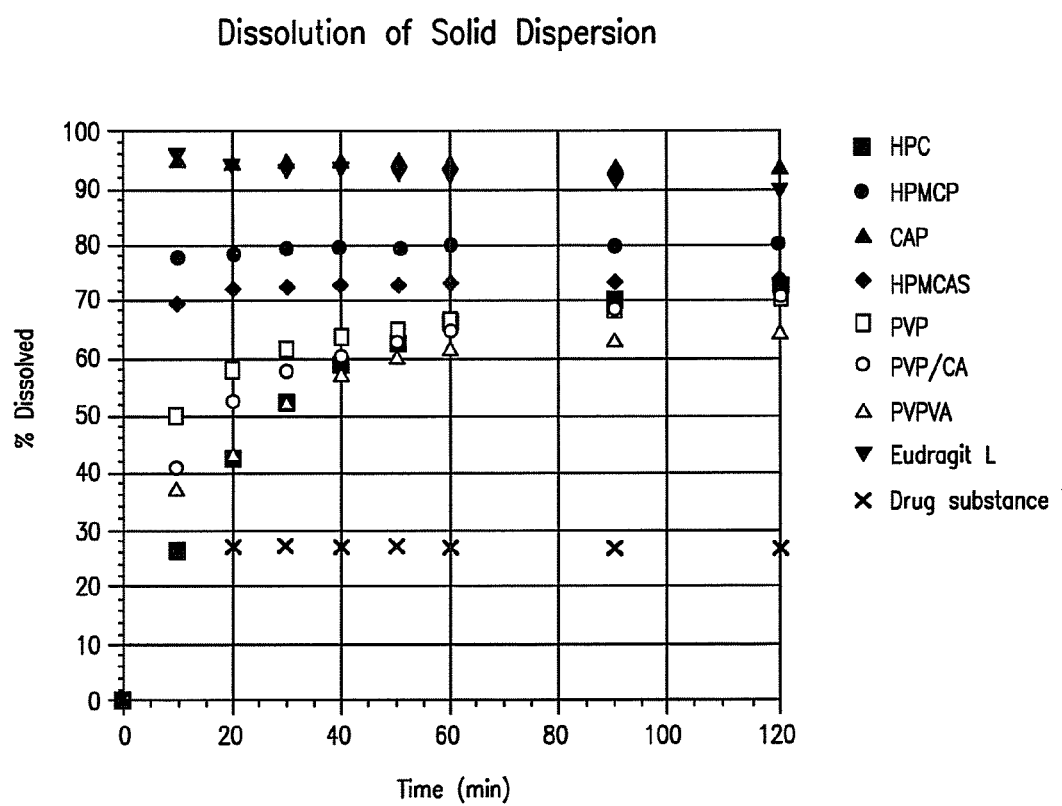
FIG. 10 shows dissolution testing results showing the solubility/dissolution rate of amorphous solid dispersions of the invention, comparative amorphous solid dispersions, and pure crystalline drug substance in aqueous 0.25% sodium lauryl sulfate/0.01 M pH 7 phosphate buffer.
Figure 11:
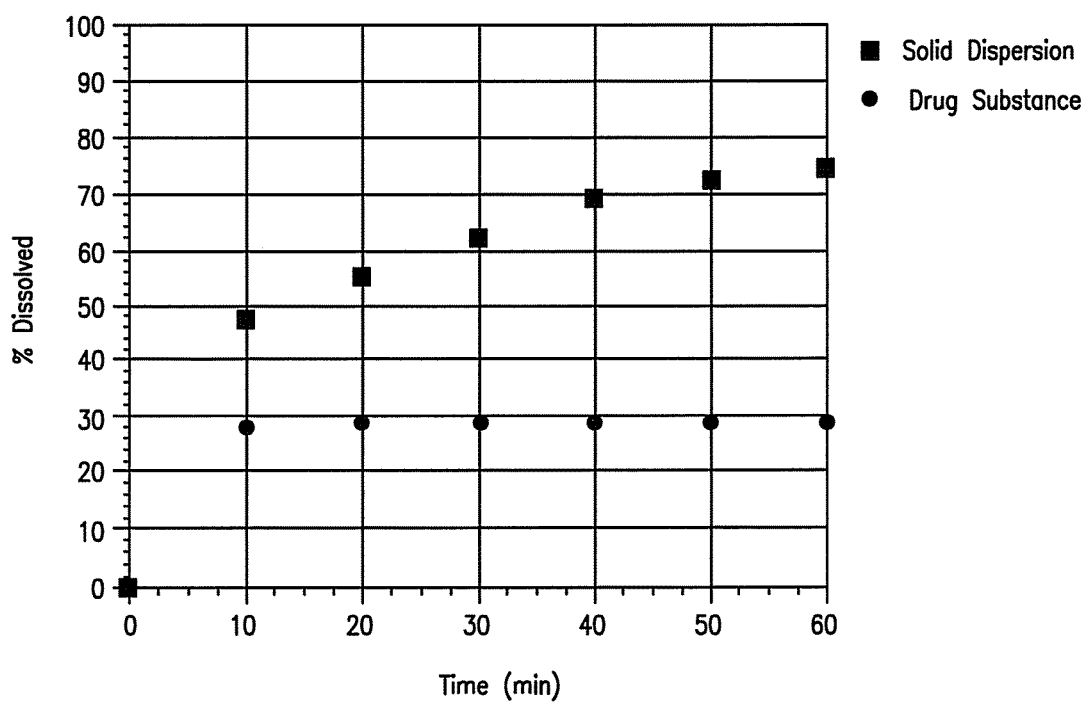
FIG. 11 shows dissolution testing results comparing the solubility/dissolution rate of an amorphous solid dispersion of 7-chloro-N,N,5-trimethyl-4-oxo-3-phenyl-3,5-dihydro-4H-pyridazino[4,5-b]indole-1-acetamide in hydroxypropyl methylcellulose phthalate of the present invention and pure crystalline drug substance in aqueous 0.25% sodium lauryl sulfate/0.01 M pH 7 phosphate buffer.

Dissolution Study (FIGS. 10 and 11)

The pure crystalline drug substance utilized in the following dissolution studies was prepared by dissolving 7-chloro-N,N,5-trimethyl-4-oxo-3-phenyl-3,5-dihydro-4H-pyridazino[4,5-b]indole-1-acetamide in hot N-methyl-2-pyrrolidinone (NMP), adding ethanol to form a precipitate, and isolating the solid.

Dissolution tests of Examples 1 to 4 and Comparative Examples 5 to 8 and pure crystalline drug substance were conducted with a paddle-type drug dissolution testing bath (available from Distek Inc.) at 75 RPM and a HP 8453 UV spectrophotometer at a wavelength of 320 nm. The following parameters were used: the drug substance concentration was 20 mg/500 ml of media, wherein the media was 0.25% sodium lauryl sulfate in water/0.01M pH 7 phosphate buffer; the temperature was 37° C.; and the sampling time was 10 minutes. Two vessels for each sample were used.

The results of dissolution testing, which are shown in FIG. 10, indicate that the amorphous solid dispersions of the present invention have significantly greater dissolution rates as compared to pure crystalline drug substance and Comparative Examples 5 to 8.

Dissolution studies were repeated for Example 9 using essentially the same procedure as described for the dissolution studies for Examples 1 to 4 and Comparative Examples 5 to 8. The amorphous solid dispersion of Example 9 showed a marked increase in dissolution rate as compared to pure crystalline drug substance. The results of this experiment are shown in FIG. 11.

Bioavailability Study

The following study was performed to determine the bioavailability of a solid dispersion formulation according to the present invention relative to a conventional formulation under fasted conditions.

A convention formulation and a solid dispersion of the present invention were prepared as follows:

| Conventional Formulation | |
|---|---|
| Material | Amount (mg/capsule) |
| Active Drug Substance (micronized) | 20 |
| Polysorbate 80 | 2.00 |
| Microcrystalline Cellulose | 125 |
| Pregelatinized Starch | 249 |
| Croscarmellose Sodium | 2.00 |
| Magnesium Stearate | 2.00 |

This conventional formulation was used as reference material and was manufactured using a standard wet-granulation process and filled into a size 0 hard gelatin capsule.

| Solid Dispersion | |
|---|---|
| Material | Amount (mg/capsule) |
| Hydroxyl propyl methylcellulose phthalate | 100 |
| Active Drug Substance | 25 |

The solid dispersion was prepared according to Example 9, above, and filled into a size 0 hard gelatin capsule.

The active drug substance in a single oral dose (100 mg) of either the Conventional Formulation (n=7) or the Solid Dispersion (n=8) was given to humans and blood samples were pulled at 0.5, 1, 1.5, 2, 3, 4, 6, 8, 12, 24, 36 and 48 hours. The samples were analyzed by LC/MS (liquid chromatography/mass spectrometry).

The results are provided in Table 3. Cmax (maximum blood concentration) and AUC (area under concentration versus time plot) were significantly higher for the solid dispersion as compared to the control conventional formulation, thus indicating the improved bioavailability of the amorphous dispersions of the present invention.

TABLE 3

Bioavailability Study Results: Blood serum levels in humans after oral administration

| | Mean (SD) | |
|---|---|---|
| Parameter | Reference Capsule (n = 7) | Solid Disp (n = 8) |
| $C_{max}$ (ng/mL) | 38.5 (18.4) | 340 (144) |
| $t_{max}$ (h)* | 6 (3.0, 36) | 2.5 (1.5, 4) |
| $AUC_{0-24}$ (ng · h/mL) | 500 (217) | 2660 (1270) |

EXAMPLE 10

Tablets and capsules containing the pharmaceutical compositions of the present invention having the following composition can be produced in a conventional manner:

| | mg per tablet or capsule |
|---|---|
| Dispersion prepared according to Example 9 | 300 |
| Microcrystalline cellulose | 80 |
| Sodium starch glycolate | 16 |
| Magnesium stearate | 4 |
| Total tablet or capsule weight | 400 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A solid dispersion comprising substantially amorphous 7-chloro-N,N,5-trimethyl-4-oxo-3-phenyl-3,5-dihydro-4H-pyridazino[4,5-b]indole-1-acetamide and a stabilizing polymer.

2. The solid dispersion according to claim 1, wherein said stabilizing polymer is one or more polymers selected from the group consisting of hydroxypropyl methylcellulose phthalate, cellulose acetate phthalate, hydroxypropyl methyl cellulose acetate succinate, and a polymethacrylate.

3. The solid dispersion according to claim 2, wherein said stabilizing polymer is hydroxypropyl methylcellulose phthalate.

4. The solid dispersion according to claim 2, wherein said stabilizing polymer is cellulose acetate phthalate.

5. The solid dispersion according to claim 2, wherein said stabilizing polymer is a polymethacrylate.

6. The solid dispersion according to claim 5, wherein the polymethacrylate is polymeric polymethacrylates.

7. The solid dispersion according to claim 1, wherein the 7-chloro-N,N,5-trimethyl-4-oxo-3-phenyl-3,5-dihydro-4H-pyridazino[4,5-b]indole-1-acetamide is present in an amount of from about 0.1% to about 30% by weight relative to the weight of the stabilizing polymer.

8. The solid dispersion according to claim 7, wherein the 7-chloro-N,N,5-trimethyl-4-oxo-3-phenyl-3,5-dihydro-4H-pyridazino[4,5-b]indole-1-acetamide is present in an amount of from about 1% to about 25% by weight relative to the weight of the stabilizing polymer.

9. The solid dispersion according to claim 8, wherein the 7-chloro-N,N,5-trimethyl-4-oxo-3-phenyl-3,5-dihydro-4H-pyridazino[4,5-b]indole-1-acetamide is present in an amount of from about 5% to about 20% by weight relative to the weight of the stabilizing polymer.

10. The solid dispersion according to claim 9, wherein the stabilizing polymer is hydroxypropyl methylcellulose phthalate.

11. The solid dispersion according to claim 1, wherein at least 80% of the 7-chloro-N, N,5-trimethyl-4-oxo-3-phenyl-3,5-dihydro-4H-pyridazino[4,5-b]indole-1-acetamide is in amorphous form.

12. The solid dispersion according to claim 11, wherein at least 90% of the 7-chloro-N, N,5-trimethyl-4-oxo-3-phenyl- 3,5-dihydro-4H-pyridazino[4,5-b]indole-1-acetamide is in amorphous form.

13. The solid dispersion according to claim 12, wherein at least 95% of the 7-chloro-N, N,5-trimethyl-4-oxo-3-phenyl-3,5-dihydro-4H-pyridazino[4,5-b]indole-1-acetamide is in amorphous form.

14. A pharmaceutical composition comprising a solid dispersion according to claim 1 and one or more pharmaceutically acceptable excipients.

15. A pharmaceutical composition comprising a solid dispersion according to claim 10 and one or more pharmaceutically acceptable excipients.

16. A method for the treatment of a disease or disorder linked to a dysfunction of peripheral-type benzodiazepine receptors, which comprises administering to a patient in need of said treatment a therapeutically effective amount of a solid dispersion according to claim 1.

17. A method for the treatment of a disease or disorder linked to a dysfunction of peripheral-type benzodiazepine receptors, which comprises administering to a patient in need of said treatment a therapeutically effective amount of a pharmaceutical composition according to claim 14.

18. A method for the treatment of a neurodegenerative disease, which comprises administering to a patient in need of said treatment a therapeutically effective amount of a solid dispersion according to claim 1.

19. A method for the treatment of a neurodegenerative disease, which comprises administering to a patient in need of said treatment a therapeutically effective amount of a pharmaceutical composition according to claim 14.

20. A method for the treatment of neuropathy, which comprises administering to a patient in need of said treatment a therapeutically effective amount of a solid dispersion according to claim 1.

21. A method for the treatment of neuropathy, which comprises administering to a patient in need of said treatment a therapeutically effective amount of a pharmaceutical composition according to claim 14.

22. A method for the treatment of cancer or tumors, which comprises administering to a patient in need of said treatment a therapeutically effective amount of a solid dispersion according to claim 1.

23. A method for the treatment of cancer or tumors, which comprises administering to a patient in need of said treatment a therapeutically effective amount of a pharmaceutical composition according to claim 14.

24. A method for the treatment of a cutaneous stress, which comprises administering to a patient in need of said treatment a therapeutically effective amount of a solid dispersion according to claim 1.

25. A method for the treatment of a cutaneous stress, which comprises administering to a patient in need of said treatment a therapeutically effective amount of a pharmaceutical composition according to claim 14.

26. A method for the treatment of rheumatoid arthritis, which comprises administering to a patient in need of said treatment a therapeutically effective amount of a solid dispersion according to claim 1.

27. A method for the treatment of rheumatoid arthritis, which comprises administering to a patient in need of said treatment a therapeutically effective amount of a pharmaceutical composition according to claim 14.

28. A method for the treatment of cardiac disease or a cardiac disorder, which comprises administering to a patient in need of said treatment a therapeutically effective amount of a solid dispersion according to claim 1.

29. A method for the treatment of cardiac disease or a cardiac disorder, which comprises administering to a patient in need of said treatment a therapeutically effective amount of a pharmaceutical composition according to claim 14.

30. A process of preparing the solid dispersion according to claim 1 comprising the steps of:
   a) dissolving 7-chloro-N,N,5-trimethyl-4-oxo-3-phenyl-3,5-dihydro-4H-pyridazino [4,5-b]indole-1-acetamide and a stabilizing polymer in a suitable solvent to form a feed solution;
   b) pumping the feed solution through an atomizer; and
   c) removing the solvent to form the solid dispersion.

31. The process according to claim 30 wherein the suitable solvent is one or more solvents selected from the group consisting of dichloromethane, chloroform, ethanol, methanol, 2-propanol, ethylacetate, acetone, and water.

32. The process according to claim 30 wherein the stabilizing polymer is selected from the group consisting of hydroxypropyl methylcellulose phthalate, cellulose acetate phthalate, hydroxypropyl methyl cellulose acetate succinate, and polymethacrylate.

33. The process according to claim 30 wherein the stabilizing polymer is hydroxypropyl methylcellulose phthalate and the suitable solvent is a 50:50 mixture by volume of dichloromethane and ethanol.

* * * * *

UNITED STATES PATENT AND TRADEMARK OFFICE
CERTIFICATE OF CORRECTION

| | | |
|---|---|---|
| PATENT NO. | : 7,713,548 B2 | Page 1 of 1 |
| APPLICATION NO. | : 12/029691 | |
| DATED | : May 11, 2010 | |
| INVENTOR(S) | : Irwin C. Jacobs et al. | |

It is certified that error appears in the above-identified patent and that said Letters Patent is hereby corrected as shown below:

In column 2, line 24, delete "TIE" and insert -- THE --, therefor.

In column 14, line 28, in claim 30, delete "pyridazino [4,5-b]indole" and insert -- pyridazino[4,5-b]indole --, therefor.

Signed and Sealed this
Eighteenth Day of January, 2011

David J. Kappos
*Director of the United States Patent and Trademark Office*